United States Patent [19]

Celmer et al.

[11] Patent Number: 4,605,624

[45] Date of Patent: Aug. 12, 1986

[54] NOCARDIA SPECIES CAPABLE OF PRODUCING NARGENICIN $C_1$

[75] Inventors: Walter D. Celmer, New London; Walter P. Cullen, East Lyme, both of Conn.; Riichiro Shibakawa, Handa; Junsuke Tone, Chita, both of Japan

[73] Assignee: Pfizer Inc., New York, N.Y.

[21] Appl. No.: 570,334

[22] Filed: Jan. 13, 1984

Related U.S. Application Data

[62] Division of Ser. No. 435,793, Oct. 21, 1982, Pat. No. 4,436,747.

[51] Int. Cl.$^4$ .................. C12N 1/20; C12R 1/365
[52] U.S. Cl. ........................... 435/253; 435/872
[58] Field of Search .................. 435/253, 872, 119

[56] References Cited

U.S. PATENT DOCUMENTS

| | | | |
|---|---|---|---|
| 4,148,883 | 4/1979 | Celmer et al. | 424/122 |
| 4,224,314 | 9/1980 | Celmer et al. | 424/122 |
| 4,351,769 | 9/1982 | Whaley et al. | 260/326.34 |
| 4,360,683 | 11/1982 | Magerlein et al. | 548/526 |
| 4,363,922 | 12/1982 | Magerlein et al. | 548/526 |

OTHER PUBLICATIONS

Celmer et al., Journal of the American Chemical Society, 102, 4203 (1980).

Whaley et al., 21st Interscience Conference on Antimicrobial Agents and Chemotherapy, Chicago, IL, Abstract No. 187, Nov. 4–6, 1981.

Tone et al., 20th Interscience Conference on Antimicrobial Agents and Chemotherapy, New Orleans, LA, Abstract No. 62, Sep. 22–24, 1980.

*Primary Examiner*—Alvin E. Tanenholtz
*Attorney, Agent, or Firm*—Charles J. Knuth; Peter C. Richardson; J. Trevor Lumb

[57] ABSTRACT

A new antibiotic substance, which has been named nargenicin $C_1$, has been isolated from fermentations of a species of the genus *Nocardia*. Nargenicin $C_1$ can be used as an antibacterial agent against susceptible bacteria, especially susceptible strains of *Staphylococcus aureus*.

2 Claims, No Drawings

NOCARDIA SPECIES CAPABLE OF PRODUCING NARGENICIN $C_1$

CROSS-REFERENCE TO RELATED APPLICATION

This application is a division of application Serial No. 435,793, filed Oct. 21, 1982, and now U.S. Pat. No. 4,436,747.

BACKGROUND OF THE INVENTION

This invention relates to a new antibiotic substance, designated CP-57,820. Said new antibiotic substance has been identified as a new member of the nargenicin family of antibiotics, and it has been named nargenicin $C_1$. Nargenicin $C_1$ has been obtained from fermentations of a new microorganism which was isolated from a soil sample collected in Georgia, U.S.A., and which has been designated culture N467-32. Culture N467-32 is considered as a member of the genus Nocardia, and it is designated as Nocardia sp.

The following nargenicins are already known:

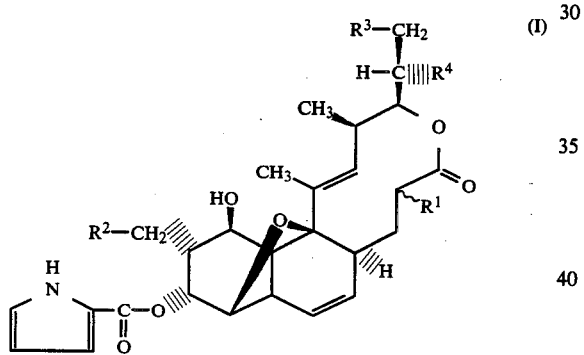

| Nargenicin | $R^1$ | $R^2$ | $R^3$ | $R^4$ |
|---|---|---|---|---|
| $A_1$ | ◂■OCH₃ | H | H | OH |
| 18-deoxy $A_1$ | ◂■OCH₃ | H | H | H |
| $B_1$ | ∥∥OH | OCH₃ | OCH₃ | OH |
| $B_2$ | ∥∥OH | OCH₃ | OH | H |
| $B_3$ | ∥∥OH | H | OCH₃ | OH |

See further, U.S. Pat. No. 4,148,883 and Celmer et al., Journal of the American Chemical Society, 102, 4203 (1980); Whaley et al., 21st Interscience Conference on Antimicrobial Agents and Chemotherapy, Chicago, IL, Abstract No. 187, Nov. 4–6, 1981; U.S. Pat. No. 4,224,314 and Tone et al., 20th Interscience Conference on Antimicrobial Agents and Chemotherapy, New Orleans, LA, Abstract No. 62, Sept. 22–24, 1980.

SUMMARY OF THE INVENTION

This invention provides a new antibiotic having the chemical structure II:

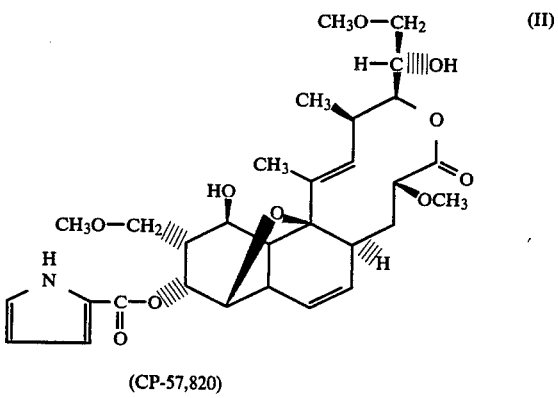

(CP-57,820)

Compound II has been named nargenicin $C_1$ and it is useful as an antibacterial agent. Nargenicin $C_1$ has been obtained by culture of a species of the genus Nocardia, designated Nocardia sp. N467-32. (ATCC 39177).

Also embraced within this invention is a method of treating a bacterial infection in a mammalian subject using nargenicin $C_1$, pharmaceutical compositions comprising nargenicin $C_1$, and biologically pure cultures of Nocardia sp. N467-32 (ATCC 39177).

DETAILED DESCRIPTION OF THE INVENTION

The antibiotic of this invention, nargenicin $C_1$, is produced by fermentation of a new microorganism designated as culture N467-32, which was obtained from a soil sample collected in Georgia, U.S.A. Culture N467-32 was characterized by Liang H. Huang, Ph.D., Pfizer Inc., Groton, Conn. U.S.A. as described hereinbelow.

Culture N467-32 was found to be gram-positive, non-acid-fast and characterized by a white aerial mycelium and a cream to yellowish substrate mycelium. The cell wall contains arabinose, galactose, mesodiaminopimelic acid and nocardomycolic acid.

An inoculum of culture N467-32 was prepared by planting from a freeze-dried lyophile into ATCC No. 172 broth and growing for four days at 28° C. on a shaker. The growth was centrifuged, washed three times with sterile distilled water, and planted on media commonly used for identification of members of the Actinomycetales. Incubation was made at 28° C. and a reading of results was made at varying times but most commonly at 14 days.

Identification media used for the characterization of the culture and references for their composition were as follows:

1. Tryptone Yeast Extract Broth (ISP #1 medium, Difco).
2. Yeast Extract—Malt Extract Agar (ISP #2 medium, Difco).
3. Oatmeal Agar (ISP #3 medium, Difco).
4. Inorganic Salts—Starch Agar (ISP #4 medium, Difco).
5. Glycerol—Asparagine Agar (ISP #5 medium, Difco).
6. Peptone—Yeast Extract Iron Agar (ISP #6, medium, Difco).
7. Gelatin Agar—R. E. Gordon and J. M. Mihm, Jr. Bact. 73:15–27, 1957).
8. Starch Agar—Ibid.

9. Organic Nitrate Broth—Ibid.
10. Dextrose Nitrate Broth—S. A. Waksman, The Actinomycetes, Vol. 2, medium no. 1, p. 328, 1961, and 3 g dextrose substituted for 30 g sucrose and agar omitted.
11. Potato Carrot Agar—M. P. Lechevalier, Jr. Lab. and Clinical Med. 71:934–944, 1968 but use only 30 g potatoes, 2.5 g carrots and 20 g agar.
12. 2% Tap Water Agar.
13. Czapek-Sucrose Agar—S. A. Waksman, The Actinomycetes, Vol. 2, medium no. 1, p. 328, 1961.
14. Glucose-Asparagine Agar—Ibid, medium no. 2, p. 328.
15. Glucose-Yeast Extract Agar—Ibid, Medium no. 29, p. 331.
16. Emerson's Agar—Ibid, medium no. 28, p. 331.
17. Nutrient Agar—Ibid, medium no. 14, p. 330.
18. Bennett's Agar—Ibid, medium no. 30, p. 331.
19. Gordon and Smith's Tyrosine Agar—R. E. Gordon and M. M. Smith, Jr. Bact. 69:147–150, 1955.
20. Casein Agar—Ibid.
21. Calcium Malate Agar—S. A. Waksman, Bact. Rev. 21:1–29, 1957.
22. Skim Milk—Difco.
23. Cellulose Utilization—
   (a) H. L. Jensen, Proc. Linn, Soc. N.S.W. 55:231–248, 1930.
   (b) M. Levine and H. W. Schoenlein, A Compilation of Culture Media, medium 2511, 1930.
24. Utilization of Organic Acids—R. E. Gordon et al., Int. Jr. Syst. Bact. 24:54–63, 1974.
25. Carbohydrate Utilization and Acid Production from Carbohydrates—Ibid.
26. Hydrolysis of Hippurate and Esculin—Ibid.
27. Decomposition of Adenine, Hypoxanthine, Xanthine, and Urea—Ibid.
28. Resistance to Lysozyme—Ibid.
29. ISP #2 Medium plus 50 ml Coconut Milk for studies of Temperature and Survival at 50° C.

Culture N467-32 exhibited the following characteristics, with colors being given in common terminology and also with reference to color chips from the *Color Harmony Manual*, 4th Edition.

The methods used for whole-cell and sugar analyses were those described in Becker, B. et al. Appl. Microbiol. 12:421–423, 1964; and in Lechevalier, M. P., J. Lab. Clin. Med. 71:934–944, 1968. About 54 grams of autoclaved, wet mycelium were used for mycolate analyses, using the method described by Lechevalier, M. P. et al. in J. Bacteriol, 105:313–318, 1971. For the purpose of comparisons, cultures of *Nocardia argentinensis* Huang ATCC 31306 (U.S. Pat. No. 4,148,883, Apr. 10, 1979), *N. paraffinae* (Jensen) Waksman & Henrici ATCC 21509, and *N. Otitidis-caviarum* Snijders ATCC 14629 were used.

Yeast Extract-Malt Extract Agar—Growth good, cream to tan (2ea, near 2gc), raised, wrinkled to slightly roughened, with white aerial mycelium; reverse yellowish (2ic); no soluble pigment.
Oatmeal Agar—Growth poor to moderate, off-white, thin, smooth, aerial mycelium short, off-white; reverse off-white; no soluble pigment.
Inorganic Salts-Starch Agar—No growth.
Glycerol-Asparagine Agar—Growth poor to moderate, off-white to cream (1½ca), thin, smooth, aerial mycelium cream; reverse same as surface; no soluble pigment.
Glucose-Asparagine Agar—Growth good, cream to yellowish (2ca, 2ea), raised, smooth to wrinkled, aerial mycelium white; reverse yellowish (2ea); no soluble pigment.
Czapek-Sucrose Agar—Growth poor to moderate, cream (1½ca) thin, smooth, aerial mycelium cream; reverse cream; no soluble pigment.
Glucose-Yeast Extract Agar—Growth good, yellowish (2ea), raised, wrinkled, aerial mycelium none to sparse, white; reverse yellowish (2ga); no soluble pigment.
Emerson's Agar—Growth moderate to good, yellowish (near 2ea), moderately raised, slightly wrinkled, aerial mycelium short and sparse, white; reverse yellowish (2ea, 2ga); no soluble pigment.
Nutrient Agar—Growth moderate, cream (1½ca, 2ca), thin to slightly raised, smooth, aerial mycelium short and sparse, white; reverse cream (2ca); no soluble pigment.
Bennett's Agar—Growth good, yellowish (2ea, 2ga), raised, wrinkled, aerial mycelium white; reverse pale yellowish (2ga); soluble pigment pale yellowish (2ea).
Gordon and Smith's Tyrosine Agar—Growth moderate to good, grayish cream (near 2ec), moderately raised, smooth to slightly wrinkled, aerial mycelium none to sparse, white; reverse yellowish (2ea); soluble pigment dark brown (4pg).
Calcium Malate Agar—Growth poor, cream (1½ca), thin, smooth, aerial mycelium cream; reverse colorless; no soluble pigment.
Casein Agar—Growth moderate, white, thin, smooth, aerial mycelium white; reverse white to cream (1½ca); no soluble pigment.
Gelatin Agar—Growth good, cream (1½ca, 2ca), raised, smooth to slightly wrinkled, aerial mycelium white; reverse cream (2ca); no soluble pigment.
Starch Agar—Growth good, cream (2ca), moderately raised, smooth to slightly wrinkled, aerial mycelium white; reverse cream (2ca); no soluble pigment.
Potato Carrot Agar—Growth poor to moderate, cream (1½ca), thin, smooth, may occur as isolated colonies, aerial mycelium cream; reverse colorless to cream; no soluble pigment.
Tap Water Agar—Growth poor, colorless to pale cream (1½ca), thin, smooth, aerial mycelium none to sparse; reverse colorless; no soluble pigment.

Morphological observations were made on culture N467-32 every day up to 15 days after the inoculation of the culture on Czapek-sucrose agar. Substrate mycelium began to fragment into bacilliary cells after 5-day incubation. After 15 days the aerial mycelium was sparse, white, branched; both the aerial mycelium and substrate mycelium sometimes fragmented into rods or long rods with the rods measuring 2–5 (or longer)×0-.6–0.8 micrometers, smooth as revealed by scanning electron microscopy.

Culture N467-32 exhibited the following biochemical properties:
I. Gram-positive; non-acid-fast; melanin production negative; production of hydrogen sulfide positive; nitrate reduction negative; gelatin liquefaction negative; hydrolysis of esculin and hippurate positive; hydrolysis of starch negative; decomposition of xanthine, adenine and casein negative; decomposition of tyrosine and urea positive; utilization of calcium malate variable; decomposition of hypoxanthine variable; decomposition of cellulose negative; no growth in Jensen's or Levine & Schoenlein's cellulose broth;

no coagulation and no peptonization on milk; resistance to lysozyme positive.

II. Utilization of organic acids: acetate, lactate, malate, propionate, pyruvate and succinate utilized; benzoate, citrate, dextrin, mucate, oxalate, phenol and tartrate not utilized.

III. Acid production from carbohydrate: Acid produced from fructose, galactose, glucose, glycerol, inositol, mannitol, raffinose, ribose, salicin, starch, sucrose and trehalose; acid not produced from adonitol, arabinose, cellobiose, dulcitol, erythritol, lactose, maltose, mannose, melezitose, melibiose, alpha-methyl-d-glucoside, rhamnose, sorbitol, sorbose and xylose.

IV. Carbohydrate utilization; Fructose, glucose, galactose, glycerol, inositol, maltose, mannitol, raffinose, ribose, salicin, starch, sucrose and trehalose utilized; mannose, melibiose, alpha-methyl-d-glucoside, sorbitol, sorbose and xylose doubtfully utilized; adonitol, arabinose, cellobiose, dulcitol, erythritol, lactose, melezitose and rhamnose not utilized.

The relationship of temperature to growth rate for culture N467-32 was as follows: 28° C., excellent growth; 21° C., good growth; 37° and 45° C., no growth. It survives at 50° C. for 8 hours.

The cell wall of culture N467-32 contains mesodiaminopimelic acid, arabinose, galactose, glucose and mannose.

Mycolate analysis revealed that the mycolates are of the nocardomycolate type.

The culture N467-32 is related to *Nocardia argentinensis, N. paraffinae* and *N. otitidis-caviarum* in most of the morphological and biochemical properties. It differs from *N. argentinensis* in the cream to yellowish substrate mycelium; the production of hydrogen sulfide; negative nitrate reduction; negative gelatin liquefaction; positive hippurate hydrolysis; negative casein decomposition; negative utilization of citrate; and acid production from galactose, mannitol, and raffinose. It differs from *N. paraffinae* in the ability to decompose tyrosine and urea, negative nitrate reduction, positive hippurate hydrolysis, acid production from inositol and raffinose, and inability to produce acid from sorbitol. When compared with *N. otitidis-caviarum*, the culture N467-32 differs in positive tyrosine decomposition, negative decomposition of xanthine and starch, negative nitrate reduction, acid production from galactose and raffinose, and inability to produce acid from mannose. Until more strains are isolated, the culture N467-32 is considered as a member of the genus Nocardia and designated as Nocardia sp. Culture N467-32 is on deposit at the American Type Culture Collection, Rockville, Md., U.S.A., under the accession number ATCC 39177. The permanency of the deposit of this culture at the American Type Culture Collection at Rockville, Md., U.S.A. and ready accessibility thereto by the public are afforded throughout the effective life of the patent in the event the patent is granted. Access to the culture is available during pendency of the application under 37 CFR 1.14 and 35 USC 112. All restrictions on the availability to the public of the culture deposited will be irrevocably removed upon granting of the patent.

The antibiotic of this invention, nargenicin $C_1$, is obtained by fermenting Nocardia sp. ATCC 39177, and extracting the nargenicin $C_1$ from the fermentation broth. Nargenicin $C_1$ can be isolated from the extract by classical methods such as chromatography or countercurrent distribution.

The Nocardia sp. ATCC 39177 culture can be grown from 24°–36° C. under submerged conditions with agitation and aeration on media consisting of carbohydrate sources such as sugars, starches, glycerol; organic nitrogen sources such as soybean meal, casamino acids, yeast extract; growth substances such as grain solubles, fish meal, cotton seed meal; mineral salts containing trace elements such as iron, cobalt, copper, zinc etc. and calcium carbonate or phosphates as buffering agents.

Inoculum is prepared by scraping vegetative cells from slants or Roux bottles inoculated with the Nocardia sp. ATCC 39177 culture. A solid medium suitable for initial growth on slants and Roux bottles is ATCC medium No. 172.

| ATCC 172 | |
|---|---|
| Ingredient | gm/liter |
| Glucose | 10 |
| Soluble Starch | 20 |
| Yeast Extract | 5 |
| NZ Amine A (Humko)* | 5 |
| Calcium Carbonate | 1 |
| Distilled Water to 1000 ml; | |
| pH to 7.0 with KOH | |
| Add Agar | 20 |

*A purified enzymatic digest of casein.

Vegetative cells from slants are used to inoculate either shake flasks or inoculum tanks; or alternately the inoculum tanks are inoculated from the shake flasks. In shake flasks, growth will generally have reached its maximum in two to four days whereas in the inoculum tanks growth will usually be at the most favorable period in one and one half to three days. A fermentor can be inoculated with vegetative broth from the inoculum flasks or tank under completely aseptic conditions and fermented for a period of two to five days. Aeration is maintained in the shake flask by agitation on a shaker or in tanks by forcing sterile air through a sparger at the rate of 0.5 to 2 volumes of air per volume of broth per minute. The speed of agitation (stirring) depends upon the type of agitator employed. A shake flask is usually run at 150 to 200 cycles per minute and a fermentor at 300 to 600 revolutions per minute. Sterility is maintained at all times. The temperature is regulated between 28° C. and 36° C. Foaming during the fermentation can be controlled with sterile antifoam such as refined soybean oil, or other suitable antifoam agents added in the makeup and as needed aseptically after inoculation.

Shaker flasks are prepared using the following medium:

| M172M | Grams/liter |
|---|---|
| Glucose | 10 |
| Soluble Starch | 20 |
| Yeast Extract BYF 300 | 5 |
| NZ amine YTT (Humko)* | 5 |
| Dipotassium Hydrogen Phosphate | 0.5 |
| Meat Meal | 5 |
| Cobalt Chloride | 0.002 |
| Calcium Carbonate | 4 |
| Tap Water to one liter; | |
| pH to 7.1–7.2 | |

*A purified enzymatic digest of casein.

The medium is distributed 40 ml per 300 ml shake flasks, and then sterilized at 120° C. and 15 p.s.i. for 30 minutes. After cooling the medium is inoculated with a vegetative cell suspension from the Nocardia sp. ATCC 39177 slant culture, grown on ATCC 172 agar medium. The flasks are shaken at 28° C. on a rotary shaker having a displacement of 1.5" to 2.5" at 150 to 200 cycles per minute (CPM) for three to four days, and then used to inoculate a four liter fermentation vessel containing two liters of one of the following media:

| NAR-1 | |
|---|---|
| Ingredient | grams/liter |
| Cerelose | 10 |
| Dextrin 700 | 20 |
| Yeast Extract | 5 |
| Polypeptone | 5 |
| Dipotassium Hydrogen Phosphate | 0.5 |
| Beef Extract | 5.0 |
| Cobalt Chloride | 0.002 |
| Calcium Carbonate | 4 |
| Water to 1 liter; pH 6.7–7.0 | |

| JLK | |
|---|---|
| Ingredient | grams/liter |
| Cerelose | 10 |
| Soybean Flour | 10 |
| Corn Starch | 5 |
| NZ Amine YTT (Humko)* | 10 |
| Dipotassium Hydrogen Phosphate | 1.0 |
| Cobalt Chloride | 0.002 |
| Water to 1 liter; pH 6.7–7.0 | |

*A purified enzymatic digest of casein.

One milliliter of L61, a silicone antifoaming agent, is added and the vessels are sealed and sterilized at 120° C. and 15 p.s.i. for 45 minutes. The pots are inoculated with one (2%) or two (4%) inoculum flasks, fermented for 2 to 5 days at 30° C., stirred at 1700 revolutions per minute (RPM) and air is sparged through the broth at one volume per volume per minute. When fermentation is complete (based on antibiotic disc assay versus *S. aureus*) the fermentors are stopped, filtered at natural pH with the aid of filter aid such as Hyflo$^R$ Super-Cel or celite or the whole broth extracted twice with $\frac{1}{3}$ to $\frac{1}{2}$ volume of a solvent such as methyl isobutyl ketone or n-butanol at natural pH. The solvent is separated from the aqueous phase by aspiration, sparkled, and concentrated in vacuo to a viscous oil. The mycelial cake once separated from the broth is discarded.

Scale-up in large fermentation is carried out by preparing shake flasks containing 0.7 liters of M172M medium. The shake flask inoculum is fermented for 3 to 4 days at 28° C., composited into two sidearm bottles and then used to inoculate a 50 gallon fermentor containing 25 gallons of JLK medium. Approximately one liter (1.0%) of inoculum is used in each tank. The fermentor, after running 3 days, is harvested (25 gallons). The whole broth is extracted with $\frac{1}{3}$ volume of methyl isobutyl ketone at natural pH, separated on a Podbielniack extractor and the solvent concentrated in vacuo to an oil.

The bioactivity of the broth from fermentation of Nocardia sp. ATCC 39177, and subsequent recovery streams, can be followed by using a sensitive strain of *Micrococcus luteus* ATCC 9341 or *Staphylococcus aureus* ATCC 6538. The components in the broth and recovery streams can be visualized by using Analtech silica gel GF plates in the following system: chloroform/acetone 3:1, or chloroform/methanol 9:1, and viewing under 254 nanometer light, or the plate can be overlayed with agar seeded with either said *S. aureus* or *M. luteus* and incubated at 37° C. for 16 hours to visualize the nargenicin $C_1$.

Nargenicin $C_1$ shows antibacterial activity, particularly against gram-positive organisms such as *Staphylococcus aureus*. This antibacterial activity can be demonstrated by measuring the minimum inhibitory concentration (MIC) of the compound against a variety of organisms, according to standard procedures. Thus, the MIC's can be measured by the procedure recommended by the International Collaborative Study on Antibiotic Sensitivity Testing (Ericcson and Sherris, *Acta. Pathologica et Microbiologia* Scandinav, Supp. 217, Section B: 64–68 [1971]), which employs brain heart infusion (BHI) agar and the inocula replicating device. Overnight growth tubes are diluted 100 fold for use as the standard inoculum (20,000–10,000 cells in approximately 0.002 ml. are placed on the agar surface; 20 ml. of BHI agar/dish). Twelve 2 fold dilutions of the test compound are employed, with initial concentration of the test drug being 50 mcg/ml. Single colonies are disregarded when reading plates after 18 hours at 37° C. The susceptibility (MIC) of the test organism is accepted as the lowest concentration of compound capable of producing complete inhibition of growth as judged by the naked eye.

The antibacterial activity of nargenicin $C_1$ makes it suitable for the treatment of bacterial infections in mammals, e.g. man, and it can be administered via the oral or the parenteral routes. In general, the antibiotic is most desirably administered in daily oral doses of 0.5 to 1 gram, or parenteral injections of 100 to 500 mg, depending on the type and severity of the infection and weight of the subject being treated.

Nargenicin $C_1$ may be administered alone or in combination with pharmaceutically-acceptable carriers, and such administration can be carried out in both single and multiple doses.

For purposes of oral administration, tablets containing various excipients such as sodium citrate, calcium carbonate and dicalcium phosphate may be employed along with various disintegrants such as starch, alginic acid and certain complex silicates together with binding agents such as polyvinyl-pyrrolidone, sucrose, gelatin and gum acacia. Additionally, lubricating agents such as magnesium stearate, sodium lauryl sulfate and talc are often useful for tableting purposes. Solid compositions of a similar type may also be employed as fillers in soft and hard-filled gelatin capsules; preferred materials include lactose as well as high molecular weight polyethylene glycols. When aqueous suspension and/or elixirs are desired for oral administration, the essential active ingredient therein may be combined with various sweetening or flavoring agents, coloring matter or dyes, and if desired, emulsifying and/or suspending agents as well, together with such diluents as water, ethanol, propylene glycol, glycerol and various combinations thereof.

For purpose of parenteral administration, solutions of nargenicin $C_1$ in sesame or peanut oil or in aqueous propylene glycol may be employed.

EXAMPLE

Isolation of Nargenicin $C_1$

The whole broth (ca 25 gallons) from a fermentation of Nocardia sp. ATCC 39177 was extracted with methyl isobutyl ketone (ca 8 gallons) at the natural pH of the fermentation. Concentration of the organic extract followed by trituration of the residue with heptane afforded 57 g of an oil.

The latter oil was dispersed on 250 g of silica gel 60 in the presence of 1.0 liter of heptane and then added to a 2.0 liter sintered glass filter coated with 500 g of silica gel 60. The silica gel was washed successively with 1.0 liter heptane, 1.0 liter heptane: chloroform 50:50, 4.0 liters of chloroform, 1.0 liter chloroform:ethyl acetate 72:25, 1.0 liter chloroform:ethyl acetate 50:50, 1.0 liter chloroform:ethyl acetate 25:75 then 4.0 liters of ethyl acetate. All steps in the purification sequence were monitored by thin-layer chromatography and by bioassay. Paper discs were dipped in solutions of known concentrations (standards) of the antibiotic and the unknown solution and the discs were dried and placed on agar seeded with *Staphylococcus aureus* ATCC 6538. The agar was incubated overnight at 37° C. and the zones of inhibition were compared. The greater part of the antibiotic activity was found in the chloroform-:ethyl acetate 50:50, 25:75 and the first two liters of ethyl acetate. These eluates were combined, concentrated and dissolved in 500 ml of ethyl acetate and then extracted v/v with 0.5M monobasic sodium phosphate, followed by 0.5M dibasic sodium phosphate buffer, finishing with water saturated with sodium chloride. The ethyl acetate was stirred with 10 g of activated carbon for thirty minutes at room temperature, filtered and concentrated in vacuo yielding 14 g of an off-white solid.

A solution of the latter material in ethyl acetate was then added to the top of a silica gel 60 column (1" dia.×96 cm) made up in heptane. A gradient from 100% heptane to 100% ethyl acetate was run and 20 cc cuts were collected from the column. Appropriate cuts from this column were combined and the resulting oil was dissolved in chloroform and added to a second silica gel 60 column (1" dia.×96 cm) made up in heptane. A gradient was run starting with chloroform to chloroform:acetone 3:1. Twenty ml cuts were combined and evaporated to an oil. After standing at room temperature overnight 800 mg of white crystals were collected. The crystals were dried under high vacuum for ca. 4 hours at 40°-50° C.

Nargenicin $C_1$ exhibited the following properties:

Infrared Spectrum (KBr disc): prominent absorptions at 2.88, 3.00, 3.40, 5.78, 5.90, 6.42, 6.90, 7.15, 7.40, 7.68, 7.82, 8.02, 8.35, 8.50, 8.90, 9.00, 9.30, 9.50, 9.90, 10.40, 11.40 and 13.40 microns.

Solubility: soluble in methanol, ethanol, chloroform, dichloromethane, acetone, methyl isobutyl ketone and ethyl acetate; insoluble in heptane and water.

Ultraviolet spectrum: $lambda_{max}^{CH3OH}$ 265 nanometers, $E_{1\ cm}^{1\%}$ 291—unchanged on the addition of acid or base.

Molecular formula: $C_{30}H_{41}NO_{10}$ (M+ 575).

Analysis (after recrystallization from chloroform/acetone).

|  | Calcd. for $C_{30}H_{41}NO_{10} \cdot CHCl_3$ | Found | Found |
| --- | --- | --- | --- |
| Carbon (%) | 53.56 | 53.57 | 53.68 |
| Hydrogen (%) | 6.09 | 6.01 | 6.10 |
| Nitrogen (%) | 2.01 | 2.16 | 2.07 |

We claim:

1. A biologically pure culture of the microorganism Nocardia sp. ATCC 39177, said culture being capable of producing nargenicin $C_1$, the compound of the formula

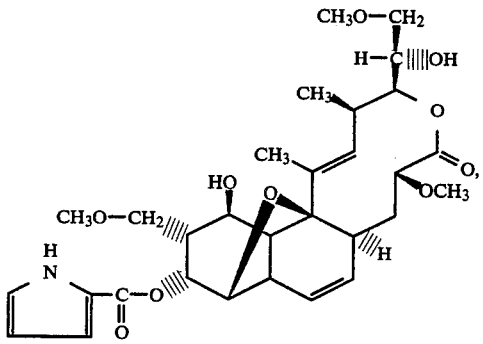

in recoverable quantity upon cultivation in an aqueous nutrient medium containing assimilable sources of carbon and nitrogen.

2. The culture of claim 1, where in freeze-dried form.

* * * * *